United States Patent [19]

Tracy et al.

[11] 4,129,739
[45] Dec. 12, 1978

[54] AMIDINE COMPOUNDS

[75] Inventors: David J. Tracy, Lincoln Park, N.J.; Walter F. Hoffstadt, Vestal, N.Y.

[73] Assignee: GAF Corporation, New York, N.Y.

[21] Appl. No.: 742,054

[22] Filed: Nov. 15, 1976

Related U.S. Application Data

[63] Continuation-in-part of Ser. No. 603,533, Aug. 11, 1975, abandoned.

[51] Int. Cl.$^2$ .............................. C07C 79/46
[52] U.S. Cl. ......................... 560/21; 548/365
[58] Field of Search .............. 260/471 A; 560/35, 21, 560/35

[56] References Cited

U.S. PATENT DOCUMENTS

| | | | |
|---|---|---|---|
| 3,798,234 | 3/1974 | Meier et al. | 260/310 A |
| C3,824,251 | 7/1974 | von Castelmur | 260/310 A |
| 3,931,221 | 1/1976 | Meier et al. | 260/310 A |
| 3,956,311 | 5/1976 | Kuffner et al. | 260/310 A |

FOREIGN PATENT DOCUMENTS 2300221  7/1974  Fed. Rep. of Germany ............. 560/35

*Primary Examiner*—Jr. Thomas
*Assistant Examiner*—G. T. Breitenstein
*Attorney, Agent, or Firm*—Walter C. Kehm; Walter Katz

[57] ABSTRACT

The amidine compounds of the invention have the general formula:

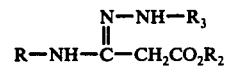

where
R$_2$ is lower alkyl,
R is phenyl substituted with halo and nitro, and
R$_3$ is selected from phenyl and phenyl substituted with one or more of halo, nitro and alkoxy, and combinations thereof which may be utilized advantageously as intermediates in the manufacture of particularly useful, high quality pyrazolone color formers which have proven especially difficult to make in high yields by other methods or techniques known in the art.

11 Claims, No Drawings

AMIDINE COMPOUNDS

This application is a continuation-in-part of application Ser. No. 603,533 filed Aug. 11, 1975, now abandoned.

BACKGROUND OF THE INVENTION

This invention relates to amidine compounds.

3-anilino-5-pyrazolones are intermediates in the manufacture of pyrazolones, such as 2-pyrazolin-5-ones, which are used as magenta color formers in photographic color materials. The 3-anilino-5-pyrazolones may be prepared by a multi-step process in which amidine compounds are formed as intermediates. Accordingly, it is an object of the present invention to provide an improved method for making amidines compounds, and more particularly to provide certain amidines which may be utilized advantageously as intermediates in the manufacture of particularly useful, high quality pyrazolone color formers which have proven especially difficult to make in high yields by other methods or techniques known in the art.

DESCRIPTION OF THE PRIOR ART

Several methods are described in the literature for preparing amidine compounds, including the patents U.S. Pat. No. 3,798,234 and British Pat. Nos. 1,129,333, 1,129,334, and 1,134,329, but these are severely limited with respect to the substituent groups which may be made a part of the amidine, or as to the yield and economy of manufacture of the desired product.

SUMMARY OF THE INVENTION

The amidine compounds of the invention have the general formula:

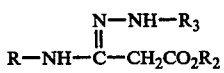

where
- $R_2$ is lower alkyl,
- R is phenyl substituted with halo and nitro, and
- $R_3$ is selected from phenyl and phenyl substituted with one or more of halo, nitro and alkoxy, and combinations thereof.

Accordingly suitable $R_3$ groups include phenyl; a nitrophenyl, such as 4-nitrophenyl and 3-nitrophenyl; a halophenyl, such as 2-chlorophenyl, 2-bromophenyl, 2,6-dichlorophenyl, 2,4,5-trichlorophenyl, 2,4,6-trichlorophenyl, 3,5-dibromophenyl and 4-fluorophenyl; and alkoxyphenyl, such as 2-ethoxyphenyl and 4-butoxyphenyl; and combinations thereof, such as a halonitrophenyl, such as 2-chloro-5-nitrophenyl and 2-chloro-4-nitrophenyl and 2-chloro-4-nitrophenyl.

In the preferred embodiment of the invention, in which R is phenyl substituted with halo and nitro, the presence of the nitro group in the amidine intermediate enables various acyl groups to be added to the molecule by reduction of the nitro group to amino and subsequent acylation. A halo substituent in the phenyl ring, which can hydrogen bond with the nitrogen atom to which the phenyl group is attached, can serve to prevent rotation of the phenyl ring, thereby decreasing the width of the absorption peak of the resultant color former compound.

DESCRIPTION OF THE PREFERRED EMBODIMENTS

A suitable starting material for preparing the amidines of the invention is an alkyl β-alkoxy-β-iminopropionate salt having the general formula:

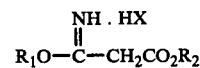

where
- $R_1$ and $R_2$ are lower alkyl, which may be same or different, and
- X is a halogen;

which may be prepared by the reaction of the corresponding nitrile with an appropriate alkanol and hydrogen halide, as described in Ber. 87, 205 (1954). Ethyl β-iminopropionate hydrogen chloride, for example, may be prepared by reaction of ethyl β-cyanopropionate, ethanol and hydrogen chloride.

The alkyl β-alkoxy-iminopropionate salt is contacted with a primary or secondary lower alkanol to form an orthoester intermediate in situ. The lower alkanol must be a non-hindered alkanol, that is, a primary or secondary lower alkanol (i.e., not a tertiary alkanol) so that the reaction between the iminopropionate and the alkanol can proceed satisfactorily to the orthoester intermediate. Both the lower alkanol and the alkoxy group of the iminopropionate may be selected from $C_1$-$C_4$ groups, which may be the same or different. Thus the three alkoxy groups of the resulting orthoester can be either all the same (e.g., trimethoxy, triethoxy, etc.) or else they can be different, depending upon the respective nature or identity of the alkoxy group and of the alkyl moiety of the alkanol reactant.

This reaction may be carried out in the alkanol reactant, which can then act as a solvent in the reaction, or preferably, in a solvent admixture which includes a high boiling component.

Reaction between the iminopropionate and alkanol is carried out at ambient temperatures, suitably at room temperature for about 12–24 hours.

Once the orthoester is formed in situ, it is directly converted to corresponding imidic ester by condensation with a suitable aniline. As a feature of the present invention, this reaction is carried out while simultaneously removing two moles of alkanol by-product from the reaction mixture, thereby providing the desired imidic ester in high yields, according to the following equations:

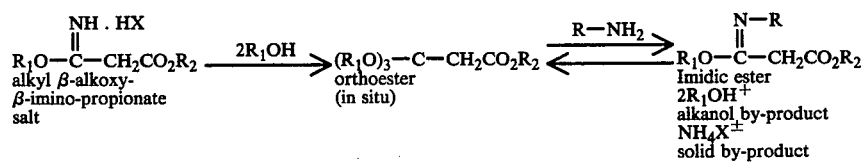

where $R_1$ and $R_2$ are as previously defined, and
$R$ is phenyl substituted with halo and nitro.

Removal of the alkanol by-product in the manner described drives the equilibrium reaction between orthoester and aniline to completion, thus substantially increasing the yield of the desired imidic ester.

As noted, condensation between the orthoester and the phenylamine preferably is carried out in the presence of a high boiling solvent for said reactants. The high boiling solvent enables the condensation reaction to proceed at an elevated temperature, and facilitates the removal of the lower boiling alkanol by-product by distillation at atmospheric pressure, thereby increasing the yield of imidic ester. Suitable high boiling solvents are those in which the reactants are inert and wholly miscible or soluble, and which have a boiling point higher than the alkanol itself, so as to enable the latter to be efficiently removed in the presence of the former. Typical solvents which satisfy these criteria have boiling points between about 80° C. and about 150° C., and are usually selected from among aromatic and aliphatic hydrocarbons and halogenated hydrocarbons, such as benzene, toluene, xylene, chlorobenzene, dichlorobenzene, tetrachloroethylene, tetrachloroethane and the like.

In a typical run, the imidic ester is formed advantageously by progressively heating the orthoester and phenylamine up to a reaction temperature of about 90°–120° C., while simultaneously removing two moles of the alkanol by-product by distillation at atmospheric pressure. Preferably, the reactants are heated up to about 110° C. during a period of about 3 or 4 hours, and then held at 110° C. for about ½ hour, during which heating periods alkanol is being distilled off continuously.

Of course, the high boiling solvent may be included initially in the charge of reactants which are used to form the orthoester, i.e., the iminopropionate and alkanol, and thus be ready for the next stage.

Solid ammonium halide, e.g., ammonium chloride, which is deposited during the course of the reaction as a by-product, then is filtered off to provide the imidic ester in the filtrate ready for the next step in the process.

Representative non-limiting examples of substituted anilines suitable for use in the first step of the process include the following: 2-chloro-4-nitroaniline; 2-chloro-5-nitroaniline; 4-chloro-2-nitroaniline; 4-chloro-3-nitroaniline; 2,5-dichloro-4-nitroaniline; 2,6-dichloro-4-nitroaniline; 4,5-dichloro-2-nitroaniline; 4-bromo-2-nitroaniline; and 4-fluoro-3-nitroaniline.

The imidic ester solution then is reacted with a phenylhydrazine to form the amidine in accordance with the following equation:

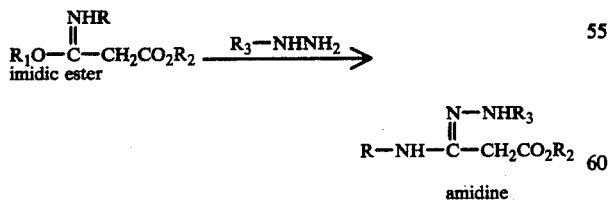

where
$R_3$ is phenyl or phenyl substituted with one or more of halo, nitro and alkoxy, and combinations thereof:
Accordingly, $R_3$ groups in the hydrazine reactant include phenyl; a halophenyl, e.g., 2-chlorophenyl, 2-bromophenyl, 2,6-dichlorophenyl, 2,4,5-trichlorophenyl, 2,4,6-trichlorophenyl, 3,5-dibromophenyl and 4-fluorophenyl; a nitrophenyl, e.g., 4-nitrophenyl and 3-nitrophenyl; and alkoxy, e.g., 2-ethoxyphenyl and 4-butoxyphenyl, and combinations thereof, such as halonitrophenyl, such as 2-chloro-5-nitrophenyl, 2-chloro-4-nitrophenyl.

The amidines thus prepared then are converted to the desired 3-anilino-5-pyrazolones by reaction with a cyclization agent which effects ring closure of the amidine. Suitably, from one to two molar equivalents of the cyclization agent is used for this purpose. The cyclization agent usually is a base, e.g., an alkali, an alkaline earth or a metal $C_1$–$C_5$ alkoxide.

Specific applications of the compositions and processes of the present invention and the various alternative embodiments thereof are further illustrated by the examples which follow. The specific details of these examples are not to be taken as limitations upon the invention.

EXAMPLE I

Ethyl β-(2,4,6-trichlorophenylhydrazone)-β-(2-chloro-5-nitroanilino) propionate

A. To flask equipped with stirrer, condenser and thermometer are charged: 97.0 g (0.5 mole) of ethyl 3-ethoxy-3-iminopropionate hydrochloride, 51.5 g (0.3 mole) of 2-chloro-5-nitroaniline, and 500 ml of anhydrous methanol. These ingredients are stirred at room temperature overnight, and the methanol is distilled off at atmospheric pressure while heating the reaction mixture up to a temperature of 105° C. The resultant salt (21.4 g) is filtered and the filter cake is washed well with methanol.

To the filtrate is added 500 ml of methanol and 58.5 g of (0.3 mole) of 2,4,6-trichlorophenylhydrazine, and this reaction mixture is refluxed overnight, and the refluxed reaction mixture cooled to 10°–15° C. and filtered, yielding 76.6 g (53% of theory) of a yellow solid, which is recrystallized from acetonitrile to yield the above-identified product having a melting point of 121°–124° C., whose structure is confirmed by infra-red and NMR spectroscopy.

Anal.: Calculated for $C_{17}H_{14}Cl_4N_4O_4$: C, 42.52%; H, 2.94%; Cl, 29.53%; N, 11.67%.
Found: C, 42.52%; H, 2.94%; Cl, 29.40%; N, 11.59%.

B. To a 5 l. flask equipped with stirrer, condenser and thermometer are charged: 730 g of ethyl-3-ethoxy-3-iminopropionate hydrochloride, 386 g of 2-chloro-5-nitroaniline, and 2500 ml of anhydrous methanol. Then 500 ml of toluene is added, and the resulting admixture is stirred 16 hours at room temperature. Then methanol is distilled off while heating the reaction mixture up to a temperature of 110° C., said temperature having been held at 110° C. for ½ hour. The ammonium chloride formed is filtered and the filter cake is washed well with methanol.

A total of 2500 ml of methanol is added to the filtrate and then 439.5 g of trichlorophenylhydrazine. The mixture is refluxed for 16 hours and cooled to room temperature to provide the desired amidine product, which is isolated from the mixture by crystallization.

EXAMPLE II

Ethyl-β-(2,4,6-trichlorophenylhydrazone)-β-(2-chloro-4-nitroaniline) propionate

The procedure of Example IB is followed using 2-chloro-4-nitroaniline in place of 2-chloro-5-nitroaniline to provide a desired amidine product.

It should be understood from the foregoing that the above description is merely illustrative of the preferred embodiments and specific examples of the present invention and that in all of which embodiments and examples, variations, such as, e.g., those previously described, can be made by those skilled in the art without departing from the spirit and purview thereof, the invention being defined by the following claims.

What is claimed is:

1. Amidines of the general formula:

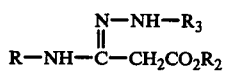

where $R_2$ is lower alkyl, and R is phenyl substituted with halo and nitro, and $R_3$ is selected from the group consisting of phenyl or phenyl substituted with one or more of halo, nitro and alkoxy and combinations thereof.

2. Amidines according to claim 1 wherein R is 2-halo-5-nitrophenyl.

3. Amidines according to claim 1 wherein R is 2-chloro-5-nitrophenyl.

4. Amidines according to claim 1 wherein R is 2-halo-4-nitrophenyl.

5. Amidines according to claim 1 wherein $R_3$ is phenyl substituted with halo.

6. Amidines according to claim 1 wherein $R_3$ is a phenyl substituted with a trihalo.

7. Amidines according to claim 1 wherein $R_3$ is 2,4,6-trichlorophenyl.

8. Ethyl β-(β-2,4,6-trichlorophenylhydrazone)-β-(2-chloro-5-nitroanilino) propionate.

9. Methyl β-(β-2,4,6-trichlorophenylhydrazone)-β-(2-chloro-5-nitroanilino) propionate.

10. Ethyl β-(β-2,4,6-trichlorophenylhydrazone)-β-(2-chloro-4-nitroanilino) propionate.

11. Methyl β-(β-2,4,6-trichlorophenylhydrazone)-β-(2-chloro-4-nitroanilino) propionate.

* * * * *